United States Patent [19]

Antonini

[11] 4,027,012
[45] May 31, 1977

[54] PROCESS FOR THE EXTRACTION OF COMPONENTS HAVING ANTICOAGULANT ACTIVITY "IN VIVO" FROM SNAKE VENOMS AND PRODUCTS OBTAINED

[75] Inventor: Eraldo Antonini, Rome, Italy

[73] Assignee: Laboratori Biochimici Fargal-Pharmasint S.p.A., Rome, Italy

[22] Filed: Apr. 5, 1976

[21] Appl. No.: 673,844

Related U.S. Application Data

[63] Continuation of Ser. No. 481,724, June 21, 1974, abandoned.

[30] Foreign Application Priority Data

Sept. 3, 1973 Italy .................................. 52309/73

[52] U.S. Cl. .................................. 424/98; 424/94
[51] Int. Cl.² ........................................ A61K 35/58
[58] Field of Search ................... 210/31 C; 424/98

[56] References Cited

UNITED STATES PATENTS

| | | | |
|---|---|---|---|
| 3,657,416 | 4/1972 | Reid et al. | 424/98 |
| 3,711,376 | 1/1973 | Hatton et al. | 424/98 |
| 3,743,722 | 7/1973 | Nolan | 424/98 |
| 3,761,586 | 9/1973 | Matsumoto et al. | 424/98 |
| 3,819,605 | 6/1974 | Holleman et al. | 424/98 |
| 3,879,369 | 4/1975 | Nolan | 424/98 |

OTHER PUBLICATIONS

Brockway et al., J. of Biological Chem., vol. 246, No. 14, Issue of July 25, 1971, pp. 4641–4647.
Björkman, Acta. Chem. Scand., 26(1972) pp. 1111–1116.
Axen et al., Acta. Chem. Scand., 25(1971) pp. 2711–2716.
Chemical Abstracts, vol. 78 (1973) 94129b & vol. 84 (1976) 131875w.

*Primary Examiner*—Donald B. Moyer
*Attorney, Agent, or Firm*—Pollock, Vande Sande & Priddy

[57] ABSTRACT

A process for extracting and isolating from snake venoms the enzymatic component having "in vitro" coagulant activity and "in vivo" anticoagulant activity from the other components having "in vitro" coagulant activity and from the protein components, wherein the snake venom, dissolved in a medium suitable for chromatographic separation treatment is passed through a column filled with a solid support for selective absorption of said in vivo anticoagulant enzyme, not soluble in aqueous solvents, bound to a substratum or inhibitor of said enzyme, a first elution medium at pH 6–7 and molarity less than or equal to 0.05M is passed through said filling, wherein said venom has been introduced, the eluate is collected in subsequent portions until the elution of more than 95% of the protein components of the venom and an "in vitro" coagulant fraction, different from that present in the second eluate are obtained, a second elution medium at a pH even greater than 9 and molarity greater than or equal to 0.3M is passed through, the eluate is collected in subsequent portions until the elution of the in vivo anticoagulant enzyme absorbed in the column, together with less than 5% of protein components are obtained, anticoagulant pharmacological preparation obtained according to the above process.

9 Claims, No Drawings

PROCESS FOR THE EXTRACTION OF COMPONENTS HAVING ANTICOAGULANT ACTIVITY "IN VIVO" FROM SNAKE VENOMS AND PRODUCTS OBTAINED

This is a continuation of application Ser. No. 481,724 filed June 21, 1974 now abandoned.

The object of the present invention is a process for the extraction of components having anticoagulant activity "in vivo" from a snake venoms and related products. More particularly, the invention concerns a process for obtaining, in a high degree of purity, the enzymatic in vivo anticoagulant components of the snake venoms by chromatographic separation techniques of the venom components.

As it is well known, the venom of several species of snakes contains enzymes having the property of catalyzing "in vitro" the gellification of the fibrinogen of the mammals' plasma and therefore of causing the coagulation of the blood, of the plasma, and of the fibrinogen solutions. However, some of these enzymes, if used in vivo, have the property of inducing a marked decrease of the fibrinogen and of causing the uncoagulability of the blood. For example the case of Ancistrodon rhodostoma venom which has coagulant properties "in vitro" and anticoagulant properties in vivo is characteristic. This fact finds an explanation on account of the presence, in the snake venoms, besides other protein components, of two types of enzymes, both endowed with coagulant activity in vitro, one of which, however, if injected in the animal blood, displays an entirely opposite action, causing the uncoagulability of the blood.

The importance is therefore evident of processes, which, like the invention process, are designed to separate the components of the snake venoms, and to isolate, in a high degree of purity, the components with anticoagulant action in vivo, which may be used, with excellent results, for the production of preparations having a pharmacological action.

Until today the separation operation of the enzymatic constituents of the snake venom has been performed by chromatography on ion exchange resins and/or with fractionating techniques by precipitation with salts or by suitable solvents.

These techniques, however, ensure neither a satisfactory degree of purity, nor a reasonable short amount of work.

Therefore, the main object of the present invention is to provide a separation process for said enzymes, which would warrant both the purity of the in vivo anticoagulant enzyme, as well as the rapidity of the operation techniques.

The process, according to the present invention, envisages the use of a chromatographic column filled with a support material not soluble in aqueous solvents, designed for the selective absorption of the in vivo anticoagulant enzyme, to which a substratum or inhibitor of said enzyme is firmly bound. When the snake venom, previously prepared for the chromatographic treatment, is passed through the column, under suitable conditions of pH and ionic strength, only the absorption of the in vivo anticoagulant enzyme is substantially effected while the other components of the venom are not absorbed. Subsequently, by elution of the support-enzyme system with solutions at a pH different from the initial one, or with solutions containing a free enzyme substratum or inhibitor, the desired enzyme is removed from the column in a high degree of purity.

Therefore, a specific object of the present invention is a process for the extraction and the isolation from the snake venoms of the enzymatic in vivo anticoagulant component from the other components having coagulant action in vitro and from protein components, characterized in that the snake venom, dissolved in a medium suitable for chromatographic treatment, is passed through a column filled with a solid support for the selective absorption of said in vivo anticoagulant enzyme, said support not being soluble in aqueous solvents, bound to a substratum or inhibitor of said enzyme then a first elution medium at pH 6–7, and with a molarity less than or equal to 0.05M, is passed through said filling, the eluate is collected in subsequent portions until more than 95% elution of the protein components of the venom, and of a fraction of the coagulant activity in vitro are obtained, a second elution medium at a pH even greater than 9 and with a molarity greater than or equal to 0.3M, is passed through, and the eluate is collected in subsequent portions until the whole amount of the in vivo coagulant enzyme absorbed by the column, together with less than 5% of the protein components is substantially obtained.

For the preparation of a product suitable for pharmacological use, said second eluate, then is diluted with water to a content of trombinic units (NIH) equal to 25 units per ml, sterilized by filtration through porous filters, a lyophilization support being added to the filtrate and the thus obtained material subdivided into 1 or 2 ml doses (25 – 50 NIH units) distributed in ampoules, is lyophilized.

According to the invention, in the case of Ancistrodon rhodostoma venom, the amino acid arginine is bound by covalent bond to the solid support filling the column, as an inhibitor of the in vivo anticoagulant enzyme. As far as the support material is concerned it is prepared according to one of the general methods already known for binding substances containing amino groups to insoluble matrixes of various types. Particularly suitable turned out to be polymer substances characteristically not soluble in aqueous solvents, containing hydroxyl groups, such as dextran gel or cellulose which have been treated with cyanogen bromide.

As previously said an arginine solution is then added to these substances activated with cyanogen bromide, with formation of a compound between the solid matrix (resin) and the arginine residue.

Particularly suitable as a support turned out to be the dextran gel prepared by the Pharmacia firm under the trade name of "Sepharose".

Now, following are some illustrative but not limitative examples of the process according to the present invention, concerning the venom of *Ancistrodon rhodostoma* (Example I) and the isolation of such in vivo anticoagulant enzyme, and also the preparation of a pharmacological product with anticoagulant action (Example II).

EXAMPLE I

Purification of the coagulant activity of the venom of *Ancistrodon rhodostoma*.

A chromatographic column with a diameter of 0.7 cm, containing 10 ml of packed gel consisting of Sepharose bound to arginine is prepared. The column is equilibrated with a Tris (hydroxymethylaminomethane)-phosphate 0.05 buffer at pH 7, hereinafter called Tris-phosphate for the sake of brevity.

50 mg of lyophilized venom of Ancistrodon rhodostoma are dissolved in 1 ml of the same buffer used to equilibrate the column. The venom solution is introduced into the column which subsequently is eluted with the Tris-phosphate 0.05M buffer at pH 7. The eluate is collected in fractions of about 2 ml. The first 30 ml of eluate contain more than 90% of the total proteins present in the venom introduced into the column, and about 180 units of in vitro coagulant activity. (1 arbitrary unit of coagulant activity is defined, for the purposes of the following experiments as that amount of enzyme which produces the initial, visible formation of fibrin fibers, under stirring, in 15 seconds at room temperature, in a 0.5% solution of human fibrinogen; this unit is different from the N.I.H. unit already mentioned before, and defined as thrombinic unit according to the N.I.H. standard). After the passage of the first 30 ml of eluate, the eluting solution is changed with a 0.2M Tris-HCl buffer at pH 9.3. Then the eluate of the new buffer is collected always in portions of 2 ml. Less than 10% of the proteins present in the 50 mg of venom introduced into the column and about 420 coagulant units are contained in the first 20 ml of this new eluate.

It should be observed that:

a. the second eluate contains, therefore, the greater part of the coagulant activity and only a small fraction of the proteins of the Ancistrodon rhodostoma venom.

b. The coagulant activity present in the first eluate is different from and not convertible into that present in the second eluate as is evident from the following test.

The most active fractions with respect to coagulant activity of the first eluate in tris-phosphate 0.05M buffer at pH 7, are introduced again into the column already described in this example, equilibrated again with 0.05M buffer at pH 7.0. The elution is performed with the same buffer; the whole coagulant activity introduced into the column is eluted now in the first 20 ml; the subsequent eluate with tris-HCl 0.2M buffer at pH 9.3 this time, does not show any significant coagulant activity.

Results similar to those heretofore mentioned, have been obtained in a very great number of tests performed with the same methods used for the previously described test, in which, however, the composition of the buffers used for the first and the second elution has been varied. For the first elution, wherein the greater part of the in vitro coagulant activity is retained in the column, tris-phosphate buffers with molarity less than or equal to 0.05M and pH ranging from 6 to 7 have been used. For the second elution, which removes from the column the greater part of the in vitro coagulating activity, buffers with molarity greater than or equal to 0.3M and pH ranging from 6 to 7 or greater than 9 have been used. A specific example of the different methods of absorption and elution with respect to the previously described test is hereinafter reported.

EXAMPLE II

Purification of an in vitro coagulant activity of the Ancistrodon rhodostoma venom and completion of a preparation having in vivo anticoagulant property and suitable for therapeutical use.

A chromatographic column with a diameter of 0.7 cm, containing 10 ml of packed gel consisting of Sepharose reacted with arginine, is prepared as in the preceding example. The column is equilibrated with a 0.01M tris-phosphate buffer at pH 6.0. 500 mg of lyophilized venom of Ancistrodon rhodostoma are dissolved in 5 ml of the same buffer (0.01M tris-phosphate at pH 6) and the solution is passed through the column.

Then the column is washed by passing through 30 ml of 0.01M tris-phosphate buffer at pH 6.0. The eluate is collected in fractions of 2 ml. Then the eluting solution is changed with one consisting of 0.3M trisphosphate buffer at pH 6.0. 75 ml of the last solution are passed through the column and the eluate is collected in 2 ml fractions.

The first eluate (0.01M Tris-phosphate, at pH 6 contains more than 95% of the proteins initially present in 500 mg of venom and about 2,200 units of coagulant activity. The second eluate (0.3M Tris-phosphate at pH 6.0) contains less than 5% of the proteins initially present in the venom and 6,000 units (arbitrary units) of in vitro coagulant activity. The protein material present therein, concentrated by ultrafiltration, proves to be essentially homogeneous when analyzed with the ultracentrifuge or by electrophoresis on gel.

This second eluate is diluted with $H_2O$ until it contains 25 NIH units (N.I.H. trombinic units) per ml. Then it is sterilized by filtration through filters, of appropriate porosity, added with a suitable material which acts as a support for the lyophilization and it is lyophilized. It is convenient to lyophilize the material after distributing it in ampoules in amounts of 1 or 2 ml corresponding to 25 or 50 N.I.H. units.

The thus lyophilized material, once redissolved by addition of $H_2O$, proves to have an unchanged in vitro coagulant activity even after several months of preservation at room temperature. Injected intravenously into the rabbit in the amount of 1 N.I.H unit per kg of body weight it induces a very strong decrease or disappearance of the blood fibrinogen within a few hours, in the absence of significant collateral phenomena and secondary effects.

This is put in evidence by the following tests:

8 rabbits have been stabled, weighed and divided in 4 groups of 2 animals each. Doses of purified material equal to 1 N.I.H unit per kg of body weight, according to the activity previously determined in vitro, have been injected intravenously into each animal. The blood withdrawn after two hours after the injection proves to be uncoagulable. Other drawings of blood have been made at times 24 h, 48 h, 72 h, 96 h, according to the following schedule

| Rabbit No. | Times | Rabbit No. | Times |
|---|---|---|---|
| 1 | 24h 72h | 5 | 24h 72h |
| 2 | 48h 96h | 6 | 48h 96h |
| 3 | 24h 72h | 7 | 24h 72h |
| 4 | 48h 96h | 8 | 48h 96h |

On the withdrawn blood samples of the fibrinogenemia have been determined by gravimetric method. The obtained data follow, expressed as mg of fibrinogen per ml of plasma

| Rabbit No. | Time | mg fibrinogen/ml plasma |
|---|---|---|
| 1 | 24 h | absent |
| 3 | 24 h | absent |
| 5 | 24 h | beginning of fibrinogen formation: non measurable |
| 7 | 24 h | beginning of fibrinogen formation: non |

-continued

| Rabbit No. | Time | mg fibrinogen/ml plasma measurable |
|---|---|---|
| 2 | 48 h | 6.2 |
| 4 | 48 h | — |
| 6 | 48 h | 4.1 |
| 8 | 48 h | 4.3 |
| 1 | 72 h | 8.1 |
| 3 | 72 h | — |
| 5 | 72 h | 7.7 |
| 7 | 72 h | — |
| 2 | 96 h | 10.5 |
| 4 | 96 h | 15.6 |
| 6 | 96 h | 8.8 |
| 8 | 96 h | — |

Drawings of blood in which the fibrinogenemia has been determined with the following results have been made on other untreated rabbits

| Rabbit No. | mg fibrinogen/ml plasma |
|---|---|
| 1 | 10 |
| 2 | 16 |
| 3 | 8.4 |

Having thus described the present invention, what is claimed is:

1. In a chromatographic separation process for extracting and isolating from snake venom the enzymatic component having "in vitro" coagulant activity and "in vivo" anticoagulant activity from the other components having in vitro coagulant activity and from the protein components, wherein said snake venom is dissolved in a medium suitable for chromatographic separation, the improvement comprising:
  A. providing a column of a water-insoluble solid support for selective absorption of said in vivo anticoagulant enzyme, being a polymer substance containing hydroxyl groups and which can be bound to arginine; and having bound thereto by covalent bond, as an inhibitor of said enzyme, arginine;
  B. introducing the snake venom dissolved in said medium suitable for chromatographic separation into said column;
  C. eluting the column with a first elution medium having a pH 6–7 and molarity of 0.05 M or less;
  D. collecting eluate in subsequent portions until the elution of more than 95% of the protein components of the venom and said other components having in vitro coagulant activity are obtained;
  E. eluting the column with a second elution medium different from said first elution medium and being selected from the group of elution medium having a pH of 6–7 or greater than 9; and having a molarity of 0.3 M or greater; and elution medium containing free arginine;
  F. collecting eluate in subsequent portions until the elution of said in vivo anticoagulant enzyme absorbed in said column, together with less than 5% of protein components. are obtained.

2. Process of claim 1 wherein said polymer substance is a dextran or cellulose gel and containing hydroxyl groups being activated by cyanogen bromide; said first elution medium being a tris-(hydroxymethyl-aminomethane) phosphate buffer at pH 7 and molarity 0.05 M, or pH 6 and molarity 0.01 M; and wherein said second elution medium is a tris-HCl buffer at pH 9.3 and molarity 0.3 M.

3. Process of claim 1 wherein said polymer substance is a dextran or cellulose gel and containing hydroxyl groups being activated by cyanogen bromide; said first elution medium being a tris-(hydroxymethyl-aminomethane) phosphate buffer at pH 7 and molarity 0.05 M, or pH 6 and molarity 0.01 M; wherein said second elution medium is a tris-phosphate buffer at pH 6 and molarity 0.3 M; and wherein said snake venom is ancistrodon rhodostoma venom.

4. Process according to claim 1, wherein said polymer substance contains hydroxyl groups and is activated by cyanogen bromide.

5. Process of claim 1 wherein said snake venom is ancistrodon rhodostoma venom.

6. Process according to claim 5, wherein said Ancistrodon rhodostoma venom is lyophilized and dissolved in the same liquid medium used for the elution of the column prior to introducing said venom into said column.

7. Process according to claim 5, wherein said liquid medium used for the first elution is a tris-(hydroxymethylamino-methane)phosphate buffer at pH 7 and molarity 0.05M, or pH 6 and molarity 0.01M.

8. Process according to claim 5, wherein said second elution medium is a tris-HCl buffer at pH 9.3 and molarity 0.3M or a tris-phosphate buffer at pH 6 and molarity 0.3M.

9. High purity, in vivo anticoagulant enzyme extracted from snake venom according to a process of claim 1.

* * * * *